(12) United States Patent
Yang

(10) Patent No.: US 11,357,657 B2
(45) Date of Patent: Jun. 14, 2022

(54) FLUID-CARRYING APPLICATION

(71) Applicant: Kuo Huang Yang, Taipei (TW)

(72) Inventor: Kuo Huang Yang, Taipei (TW)

(*) Notice: Subject to any disclaimer, the term of this patent is extended or adjusted under 35 U.S.C. 154(b) by 0 days.

(21) Appl. No.: 17/527,370

(22) Filed: Nov. 16, 2021

(65) Prior Publication Data

US 2022/0071798 A1  Mar. 10, 2022

Related U.S. Application Data

(63) Continuation of application No. PCT/CN2020/096478, filed on Jun. 17, 2020.

(30) Foreign Application Priority Data

Jun. 20, 2019  (CN) .......................... 201920932735.6

(51) Int. Cl.
*A61F 5/44* (2006.01)
*A61F 5/443* (2006.01)
(Continued)

(52) U.S. Cl.
CPC .............. *A61F 5/4408* (2013.01); *A41C 3/04* (2013.01); *A41C 3/10* (2013.01); *A61F 5/443* (2013.01); *A61F 5/4407* (2013.01); *A61F 2/52* (2013.01)

(58) Field of Classification Search
CPC combination set(s) only.
See application file for complete search history.

(56) References Cited

U.S. PATENT DOCUMENTS 4,125,117 A * 11/1978 Lee ........................... A61F 2/52
                                                                450/54
4,795,464 A *  1/1989 Eberl ....................... A61F 2/52
                                                                 623/8
(Continued)

FOREIGN PATENT DOCUMENTS

CA         2 301 445         8/2001
CA         2301445 A1 *      8/2001    ............... A61F 2/52
(Continued)

OTHER PUBLICATIONS

International Search Report dated Sep. 4, 2020 in International (PCT) Application No. PCT/CN2020/096478, with English language translation.

*Primary Examiner* — Guy K Townsend
(74) *Attorney, Agent, or Firm* — Wenderoth, Lind & Ponack, L.L.P.

(57) ABSTRACT

The present invention provides a fluid-carrying application, comprising: a first sheet with a first surface and a second surface; a second sheet with a third surface and a fourth surface, wherein a part of the third surface and a part of the second surface of the first sheet are welded or adhered to at least one band-shaped region, thereby forming a first chamber having at least a first drainage port, and the inside of the chamber can communicate with the outside through the first drainage port; an adhesive layer, which is provided on the fourth surface of the second sheet; and a release layer, which covers at least a part of the adhesive layer, wherein, the first drainage port is formed at the first sheet or an open portion where the first sheet and the part adjacent to the edge of the second sheet are not welded or adhered to each other.

25 Claims, 18 Drawing Sheets

(51) Int. Cl.
  *A41C 3/04* (2006.01)
  *A41C 3/10* (2006.01)
  *A61F 2/52* (2006.01)

(56) References Cited

U.S. PATENT DOCUMENTS

| | | | | |
|---|---|---|---|---|
| 4,899,764 A * | 2/1990 | Gauger | A61F 2/12 | 128/899 |
| 5,176,663 A * | 1/1993 | Svedman | A61F 13/0203 | 128/888 |
| 5,480,430 A * | 1/1996 | Carlisle | A61F 2/12 | 623/7 |
| 5,935,164 A * | 8/1999 | Iversen | B29C 41/22 | 623/8 |
| 6,685,681 B2 * | 2/2004 | Lockwood | A61F 13/0216 | 604/305 |
| 7,524,315 B2 * | 4/2009 | Blott | A61M 27/00 | 604/543 |
| 7,618,382 B2 * | 11/2009 | Vogel | A61M 1/90 | 601/7 |
| 7,625,362 B2 * | 12/2009 | Boehringer | A61M 1/90 | 604/305 |
| 7,723,560 B2 * | 5/2010 | Lockwood | A61F 13/0246 | 602/45 |
| 7,776,028 B2 * | 8/2010 | Miller | A61F 13/0216 | 604/543 |
| 8,235,955 B2 * | 8/2012 | Blott | A61M 1/75 | 604/305 |
| 8,394,118 B2 * | 3/2013 | Jones | A61B 90/02 | 606/192 |
| 8,500,776 B2 * | 8/2013 | Ebner | A61M 1/90 | 606/213 |
| 8,721,629 B2 * | 5/2014 | Hardman | A61M 1/90 | 604/543 |
| 8,764,732 B2 * | 7/2014 | Hartwell | A61F 13/00068 | 604/543 |
| 8,784,486 B2 * | 7/2014 | Schuessler | A61F 2/12 | 623/8 |
| 8,791,315 B2 * | 7/2014 | Lattimore | A61M 1/90 | 602/46 |
| 8,951,235 B2 * | 2/2015 | Allen | A61M 1/743 | 604/319 |
| 10,052,190 B2 * | 8/2018 | Chitre | A61F 2/12 | |
| 10,124,098 B2 * | 11/2018 | Dunn | A61F 13/022 | |
| 2001/0029956 A1 * | 10/2001 | Argenta | A61F 13/0246 | 128/897 |
| 2002/0099442 A1 * | 7/2002 | Niino | A61F 2/78 | 623/7 |
| 2002/0161346 A1 * | 10/2002 | Lockwood | A61M 1/0058 | 604/315 |
| 2004/0162512 A1 * | 8/2004 | Liedtke | A61F 13/0213 | 602/59 |
| 2007/0032763 A1 * | 2/2007 | Vogel | A61M 1/0058 | 604/305 |
| 2007/0038172 A1 * | 2/2007 | Zamierowski | A61M 27/00 | 604/20 |
| 2007/0118096 A1 * | 5/2007 | Smith | A61M 1/85 | 604/541 |
| 2008/0108977 A1 * | 5/2008 | Heaton | A61M 1/743 | 604/543 |
| 2008/0248718 A1 * | 10/2008 | Henke | A41C 3/04 | 450/38 |
| 2009/0043268 A1 * | 2/2009 | Eddy | A61M 1/74 | 604/290 |
| 2009/0069760 A1 * | 3/2009 | Finklestein | A61M 1/73 | 604/305 |
| 2009/0099519 A1 * | 4/2009 | Kaplan | A61B 46/00 | 604/113 |
| 2009/0105670 A1 * | 4/2009 | Bentley | A61F 13/0289 | 604/290 |
| 2009/0299303 A1 * | 12/2009 | Seegert | A61M 27/00 | 604/290 |
| 2010/0022990 A1 * | 1/2010 | Karpowicz | A61M 1/80 | 604/543 |
| 2010/0028407 A1 * | 2/2010 | Del Priore | A61P 17/02 | 424/443 |
| 2010/0137775 A1 * | 6/2010 | Hu | A61M 1/732 | 602/54 |
| 2010/0160874 A1 * | 6/2010 | Robinson | A61M 1/90 | 604/313 |
| 2010/0262126 A1 * | 10/2010 | Hu | A61M 1/882 | 604/543 |
| 2010/0305490 A1 * | 12/2010 | Coulthard | A61F 13/022 | 602/43 |
| 2011/0077605 A1 * | 3/2011 | Karpowicz | A61M 1/964 | 604/318 |
| 2011/0106026 A1 * | 5/2011 | Wu | A61M 1/962 | 604/319 |
| 2011/0178451 A1 * | 7/2011 | Robinson | A61F 13/00991 | 602/46 |
| 2011/0282309 A1 * | 11/2011 | Adie | A61F 13/0209 | 604/319 |
| 2012/0029455 A1 * | 2/2012 | Perez-Foullerat | A61F 13/0276 | 604/368 |
| 2012/0130327 A1 * | 5/2012 | Marquez Canada | A61F 13/0216 | 604/319 |
| 2012/0209226 A1 * | 8/2012 | Simmons | A61F 13/0246 | 604/319 |
| 2013/0110058 A1 * | 5/2013 | Adie | A61M 1/74 | 604/319 |
| 2014/0088455 A1 * | 3/2014 | Christensen | F16K 17/00 | 600/561 |
| 2014/0180225 A1 * | 6/2014 | Dunn | A61F 13/00068 | 604/319 |
| 2015/0112311 A1 * | 4/2015 | Hammond | A61F 15/008 | 604/543 |
| 2015/0150729 A1 * | 6/2015 | Dagger | A61M 1/90 | 604/543 |
| 2016/0022885 A1 * | 1/2016 | Dunn | A61M 1/90 | 604/319 |
| 2019/0358080 A1 * | 11/2019 | Yang | A61B 10/007 | |

FOREIGN PATENT DOCUMENTS

| | | |
|---|---|---|
| CN | 1365652 | 8/2002 |
| CN | 107874790 | 4/2018 |

* cited by examiner

FLUID-CARRYING APPLICATION

CROSS-REFERENCE TO RELATED APPLICATIONS

This application claims the benefit of priority to International Patent Application No. PCT/CN2020/096478, filed Jun. 17, 2020, which claims priority to Chinese Patent Application No. 201920932735.6, filed Jun. 20, 2019, each of which is incorporated by reference herein in their entirety.

TECHNICAL FIELD

The present invention relates to a fluid-carrying application, and more particularly to a fluid-carrying application that can flatter body figures, introduce fluid for personal care/medical use, or collect body fluids.

BACKGROUND

Human survival rely greatly on fluids, especially air and water. For human bodies, fluids sometimes are necessities, while sometimes are burdens. Fluids are needed by human bodies in some situations such as urinalysis, breast augmentation, skin care, wound care, cooling or keeping warm, staying hydrated, breastfeeding, etc. Fluids are a burden to human in some situations such as treating body fluids (breast milk, urine, semen, blood), etc.

Although there have been several solutions for the need or the burden between fluids and human bodies, there are still many deficiencies. For example, as for satisfying human's needs, such as for flat-chested females, bra pads would easily shift, NuBras would lose adhesiveness after repeatedly used, and surgery implanting fluids (saline implants, silicone implants) is painful and expensive. As for relieving burden, for example, babies and bedridden females would face the pain of urinary catheterization and the risk of infection when collecting urine, people with urinary incontinence would feel discomfort when wearing diapers, or face difficulties using each kind of urine collection bag which causes the leakage of urine.

SUMMARY

In view of the above problems, the present invention provides a fluid-carrying applications to temporarily keep fluids on body surfaces, which is easy to adhere to human bodies and does not easily peel off. The present invention is capable of collecting various fluids such as water, air, skin care products, liquid medicine, milk, urine, semen, or blood without leakage, meanwhile meeting human's demands for fluids and releasing the burden of fluids for human bodies. The present invention provides a simple structure, which is easy to use and low-cost. The application of the present invention may be widely used and can process the relationship between human bodies and fluids properly.

To achieve the above objectives, the present invention provides a fluid-carrying application, comprising a first sheet, provided with a first surface and a second surface; a second sheet, provided with a third surface and a fourth surface, a part of the third surface and a part of the second surface of the first sheet are welded or adhered to at least one band-shaped region, thereby forming a first chamber having at least a first drainage port, and the inside of the chamber can communicate with the outside through the first drainage port; an adhesive layer, provided on the fourth surface of the second sheet; and a release layer, covering at least a part of the adhesive layer, wherein the first drainage port is formed at the first sheet or an open portion where the second surface of the first sheet and the third surface adjacent to the edge of the second sheet are not welded or adhered to each other. Optionally, a structure support unit is further provided, which extends along the edge of the first sheet or the second sheet.

According to one embodiment of the present invention, a third sheet is provided between the first sheet and the second sheet, a second chamber is formed between the third sheet and the second sheet, and edges of the third sheet may be welded or adhered in between the first sheet and the second sheet at the same time, or to the first sheet, or to the second sheet.

According to one embodiment of the present invention, the edge of the second sheet is larger than the outer edge of the band-shaped region, and there is a distance between the outer edge of the band-shaped region and the edge of the second sheet.

According to one embodiment of the present invention, the fluid-carrying application further comprises a fifth sheet, a part of the fifth sheet is connected to the surface of the first sheet and provided with a liftable part, the liftable part is larger than the first drainage port and can fully cover the first drainage port.

According to one embodiment of the present invention, the first drainage port comprises a first liftable part of the first sheet, and the surface of the first sheet further comprises a sixth sheet, the edge of the sixth sheet is connected to the first sheet in an enclosed manner in a form of surrounding the first liftable part of the first sheet or connected to the first sheet and the second sheet at the same time and comprises an opening, with the opening being smaller than the first liftable part of the first sheet and may be fully covered by the first liftable part.

According to one embodiment of the present invention, the fluid-carrying application further comprises a drainage portion, which is connected to the first drainage port or the opening of the sixth sheet. Optionally, the drainage portion further comprises a non-return structure, which prevents the fluid from flowing from the inside of the first chamber to the outside through the drainage portion or from the outside of the first chamber to the inside. Optionally, the drainage portion is a drainage tube, which is being set up corresponding to the first drainage port or the opening of the sixth sheet. Optionally, the drainage tube is formed by combining two side edges of two seventh sheets, so that the drainage tube is flat in a natural state.

According to one embodiment of the present invention, the inner surface of the drainage portion is provided with an isolation material, which is sandwiched, coated or printed before the drainage portion is formed.

According to one embodiment of the present invention, the drainage portion is a drainage bag, which is being set up corresponding to the first drainage port or the opening of the sixth sheet. Optionally, the drainage bag is formed by sealing all or part of the edges of the two seventh sheets, or by folding an eighth sheet in half and sealing all or part of the edges of the eighth sheet. Optionally, the first sheet comprises a first liftable part; the drainage bag comprises a second liftable part that is larger than the first liftable part; the first sheet is connected to the drainage bag in an enclosed manner in a form of surrounding the first liftable part and the second liftable part; and the first liftable part is connected to a part of the second liftable part. Optionally, the fluid-carrying application further comprises a belt loop sheet, which is connected to the outer side of the drainage bag and thereby forming a passage for a fixing belt to pass through.

According to one embodiment of the present invention, the first sheet comprises an extending portion, which can be used as the seventh sheet or the eight sheet, or may be reversely folded into a belt.

According to one embodiment of the present invention, the edge of the first sheet or the second sheet is provided with a fastener in order to connect to another fluid-carrying application.

According to one embodiment of the present invention, the first sheet or the second sheet is provided with petaloid edges or undulating edges for better attaching on non-planar surfaces.

According to one embodiment of the present invention, the second sheet comprises at least a second drainage port, so that the inside of the first chamber or the inside of the second chamber can communicate with the outside through the second drainage port. A distance is provided between the second drainage port and the inner edge of the band-shaped region. The size of the second drainage port is not particularly limited, for example, the size can be a larger opening for connecting to glans penis, female's pudendum and nipples, or a smaller opening simply for fluids flow. Optionally, this embodiment further comprises a structure support unit of the drainage port, which extends along the edge of the second drainage port with an adhesive strength weaker than the adhesive layer. Optionally, this embodiment further comprises an air-permeable or liquid-permeable sheet, which is set up at the second drainage port. Alternatively, a plurality of small and densely arranged second drainage ports are processed and formed at at least a part of the second sheet. Optionally, this embodiment further comprises a second drainage tube, which is connected to the second drainage port.

According to one embodiment of the present invention, a vibration device or a discharge device is further provided, which is set up at the first sheet.

DETAILED DESCRIPTION

Figure 1:
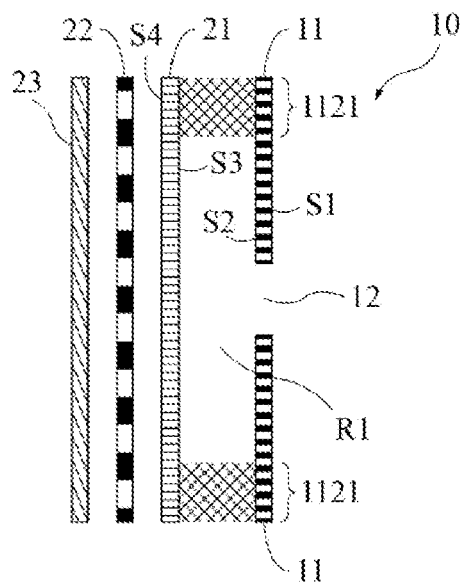
FIG. 1 is a schematic diagram of the fluid-carrying application according to the present invention.

Specific implementations of the present invention are described below with reference to the accompanying drawings, wherein the same or similar components are denoted by the same reference numerals.

FIG. 1 is an embodiment of the present invention. The fluid-carrying application 10 comprises a first sheet 11 with at least a first drainage port 12, with the first sheet 11 having a first surface S1 and a second surface S2, and a second sheet 21 having a third surface S3 and a fourth surface S4. A part of the third surface S3 and a part of the second surface S2 of the first sheet 11 are connected (welded or adhered) to at least a band-shaped region 1121, thereby forming a first chamber R1 having at least an opening which may store fluids. The inside of the first chamber R1 can communicate with the outside through the first drainage port 12. The edge of the first sheet 11 and the edge of the second sheet 21 may, but not limited to, align with each other. An adhesive layer 22 is set up at the fourth surface S4 of the second sheet 21 for adhesion to a user, and to attach the fluid-carrying application 10 to the body surface. A release layer 23, which covers at least a part of the adhesive layer 22, and prevents the adhesive layer 22 from losing the adhesiveness due to staining before use. The release layer 23 may be, for example, a release paper.

The fluid-carrying application 10 may be made of, for example, but not limited to, natural latex, synthetic latex, rubber, silicone, polyisoprene (PI), polyurethane (PU), polyethylene (PE), polyvinyl chloride (PVC), a polymer material, a biomaterial or a synthetic DNA material. The material constituting the adhesive layer 22 may include, for example, a pressure-sensitive adhesive, which is used for the adhesion of the second sheet 21 on the user's skin through the adhesive layer 22. The second sheet 21 may also be made of a viscous material. The second surface S2 of the first sheet 11 and the third surface S3 of the second sheet 21 are interconnected. The interconnection may be achieved by adhesion using such as, but not limited to, a solvent, an adhesive, a tape, or a glue film, or may be welded and connected by, for example, but not limited to, electric heating, ultrasonic, or high-frequency welding.

The first sheet 11 and the second sheet 21 may be soft sheets in natural state, which may be preferably made of an elastic material, yet an inelastic material may also be used. The thickness of the first sheet 11 and the second sheet 21 is preferably no more than 0.1 mm. The first sheet 11 and the second sheet 21 may be fabricated as a flat or arc-surface film, and the edge may be in the shape of, but not limited to, a circle, an ellipse, a rounded regular polygon, or in any shape. Preferably, the first sheet 11 is a water-proof sheet, such as a thermoplastic polyurethane (TPU) film. The second sheet 21 which is configured for adhesion to the user's skin requires better air permeability and may be made of a microporous film, such as, but not limited to, a highly air/water-permeable polyurethane (PU) film. The thickness of the second sheet 21 is preferably less than 0.1 mm, more preferably less than 0.05 mm, and most preferably less than 0.03 mm. The air permeability of the second sheet 21 is preferably with a moisture vapor transmission rate (MVTR)

greater than or equal to 500 g/(m²·24 h), and the water permeability after gumming thereof is preferably greater than or equal to 1000 g/(m²·24 h). To improve comfort and the compatibility with the skin, any material may be attached to the first surface S1 of the first sheet 11, such as woven materials, nonwoven materials or films. For ease of understanding the structures of the sheets, most of the following drawings are shown in sectional views and in exemplary forms with the chamber full of fluids.

Figure 2A:
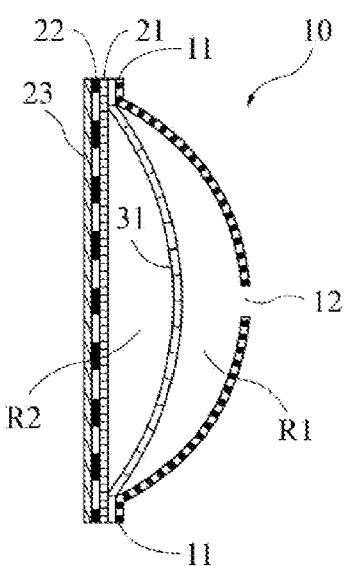
FIG. 2A to FIG. 2C are schematic diagrams of another embodiment of the fluid-carrying application.
Figure 2B:
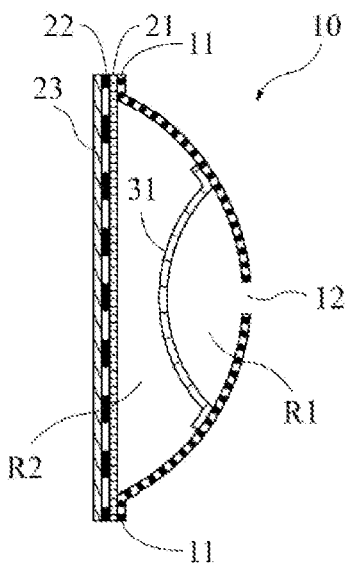
Figure 2C:
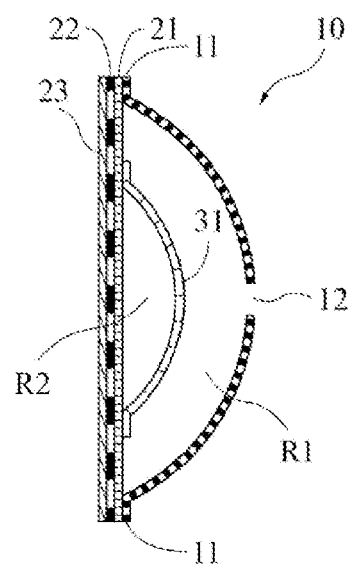

FIG. 2A to FIG. 2C are another embodiment of the present invention. Between the first sheet 11 and the second sheet 21 of the fluid-carrying application 10 is provided with a third sheet 31, thereby forming a second chamber R2 between the third sheet 31 and the second sheet 21. The edge of the third sheet 31 may be welded/adhered in between the first sheet 11 and the second sheet 21 at the same time (as shown in FIG. 2A), or welded/adhered to the first sheet 11 (as shown in FIG. 2B), or welded/adhered to the second sheet 21 (as shown in FIG. 2C). The first chamber R1 and the second chamber R2 may be injected with the same or different fluids, respectively.

Figure 3:
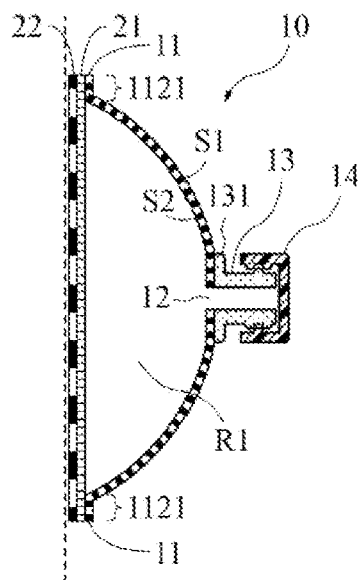
FIG. 3 is a schematic diagram of another embodiment of the fluid-carrying application.

FIG. 3 is another embodiment of the present invention, which may be used for ice packs/warm compresses. The first drainage port 12 at the first sheet 11 further comprises a drainage portion, which is connected to the first drainage port 12, and enables the inside of the first chamber R1 to connect with outside through the first drainage port 12 and the drainage portion. The first drainage port 12 may also be formed by an open portion of the connecting part, which was formed by overlapping and connecting the edges of the two first sheet 11. In the present embodiment, the first sheet 11 and the second sheet 21 are thermoplastic films. The edges of the first sheet 11 and the second sheet 21 are heat seal processed to form a band-shaped region 1121 in a continuously enclosed manner. The drainage portion is a drainage tube 13 being set up correspondingly to the first drainage port 12. One end of the drainage tube 13 is connected to the first sheet 11, and the first chamber R1 is in communication with outside through the first drainage port 12. The drainage tube 13 has an inner cross sectional area which is generally the same as or greater than the first drainage port 12, and the configuration may be in a manner of connecting the cross section of the tube wall of one end of the drainage tube 13 with the first surface S1 or the second surface S2 of the first sheet 11. Alternatively, as shown in FIG. 3, one end of the drainage tube 13 may be provided with a brim portion 131, which is generally perpendicular to an axial direction of the drainage tube 13 and surrounds the periphery of the drainage tube 13 (exemplarily, the two elements are herein connected integrally). The brim portion 131 is connected to the first surface S1 of the first sheet 11, thereby increasing the fitting tightness and the reliability of connection between the drainage tube 13 and the first sheet 11. The drainage tube 13 may be provided with a closed end, which is formed integrally with other parts of the drainage tube 13, such as a test tube. Alternatively, the drainage tube 13 may further comprise a cap 14 for the drainage tube 13 to be opened or closed. In the present embodiment, the drainage tube 13 extends from the first drainage port 12 to the direction opposite of the first chamber R1, and the cap 14 and the drainage tube 13 are threadedly locked with each other. When in use, the fluid-carrying application 10 is attached to a user's skin through the adhesive layer 22, cold/hot water is injected into the first chamber R1, and the drainage tube 13 is closed with the cap 14, which may help the user with icing, warm compression, physiotherapy, or keeping warm in cold weather. The drainage tube 13 may also be used to drain and exchange the water when the water temperature is similar to the body temperature. It may be understood by those of ordinary skill in the art that in this embodiment, the design may be simplified by replacing the threads with a flange provided on one of the cap 14 and the drainage tube 13 and a concave flange provided on the other, so that the two may be fixed with each other.

Figure 4:
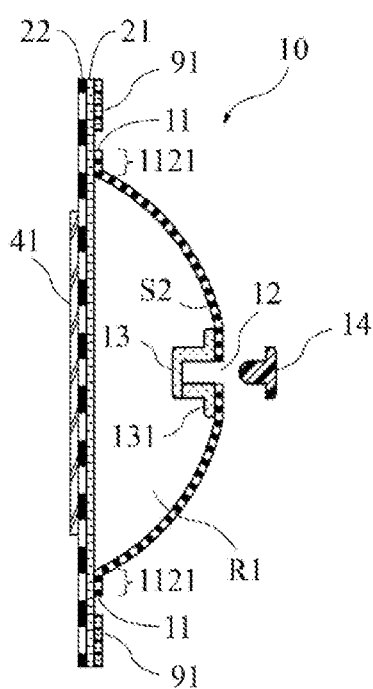
FIG. 4 is a schematic diagram of another embodiment of the fluid-carrying application.

FIG. 4 is another embodiment of the present invention, which may achieve the effect of increasing a female's breast size visually after wearing clothes. The brim portion 131 of the drainage tube 13 is connected to the second surface S2 of the first sheet 11. The drainage tube 13 extends from the first drainage port 12 to the direction of the first chamber R1 for fluid injection. After the injection of water, upon closing the drainage tube 13 with the cap 14, the fluid in the first chamber R1 would be drained due to pressure or gravity. As a result, the drainage tube 13 may further comprise a non-return structure to prevent the fluid from flowing from the inside of the first chamber R1 to outside through the drainage tube 13. The first chamber R1 is formed by connecting the first sheet 11 and the second sheet 21 with the continuously enclosed band-shaped region 1121. Especially the first chamber R1 which is made of soft sheets, would expand like a pillow from the periphery to the center when being full of fluids, and the pressure of the fluids would make the edges of the second sheet 21 peel off easily from the body surface. To solve the above problems, the edge of the second sheet 21 may be larger than the outer edge of the band-shaped region 1121 or the edge of the first sheet 11, thereby forming a distance between the outer edge of the band-shaped region 1121 and the edge of the second sheet 21, wherein the widest part of the distance is preferably greater than 3 mm, more preferably greater than 8 mm, most preferably greater than 15 mm, so as to improve the fitting of the periphery of the fluid-carrying application 10. Such as a tent that is secured to the ground with ropes and tent stakes, the radially protruded second sheet 21 (such as a rope) may better attach a surface of the first chamber R1 that is adjacent to the second sheet 21 on the body surface through the adhesive layer 22 (such as a tent stake). Furthermore, setting the inner edge of the band-shaped region 1121 as the reference point, the effect of bilateral fix at the inner side and the outer side of the second sheet 21 is achieved by the adhesive layer 22, and effectively prevents the second sheet 21 from peeling off from the body surface due to excessive tensile force or hydraulic pressure applied on the first sheet 11. In addition, since the second sheet 21 is larger than the outer edge of the band-shaped region 1121 (that is, there is a distance between the edge of the second sheet 21 and the outer edge of the band-shaped region 1121), the total thickness gradually increases from the edge to the center. Comparing to the configuration shown in FIG. 1 to FIG. 3 where the thicker (two layers) edge is formed by the first sheet 11 and the second sheet 21 aligning with each other, and the thicker edge is easily rolled up due to friction, the thinner edge may better prevent the periphery of the fluid-carrying application 10 from peeling off due to friction. The present invention may further comprise a structure support unit 91, which extends along the edge of the first sheet 11 or the second sheet 21, functioning as a frame being set up at the first sheet 11 or the second sheet 21, in order to maintain the shape of the edge before adhesion and prevent the formation of folds. After adhesion, the user may remove the structure support unit 91. In the present embodiment, the second sheet 21 for adhesion to a breast is a flat film, while the first sheet 11 is preferably made of an arc-surface film, thereby increasing the volume of the first chamber R1 and can increase the breast size visually. Additionally, a fourth sheet 41 may be set up at least a part of the adhesive layer 22 for sweat absorption. The fourth sheet 41 is an absorbent sheet comprising fibers, pores, or water absorbing polymeric materials, such as but not limited to tissue papers, cottons, gauzes, non-woven fabrics, sponges, or artificial skin. The edge of the fourth sheet 41 does not extend beyond the inner edge of the band-shaped region 1121. Apart from increasing the size of breast shape visually, one may flatter figures of other parts using the same methods, such as but not limited to the plantar arc of a flat foot.

Figure 5A:
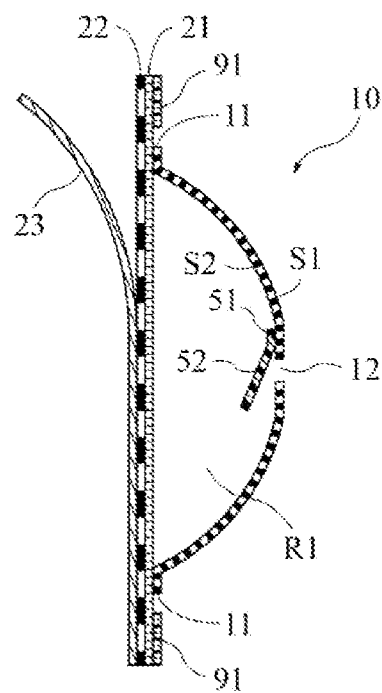
FIG. 5A to FIG. 5E are schematic diagrams of another embodiment of the fluid-carrying application.
Figure 5B:
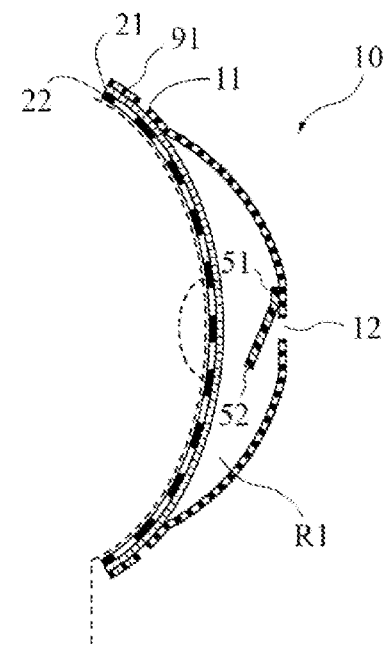
Figure 5C:
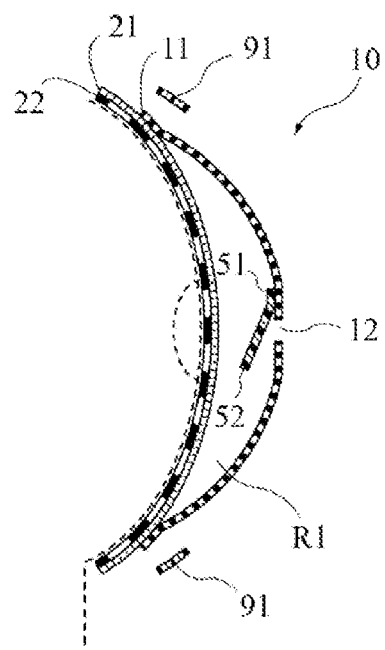
Figure 5D:
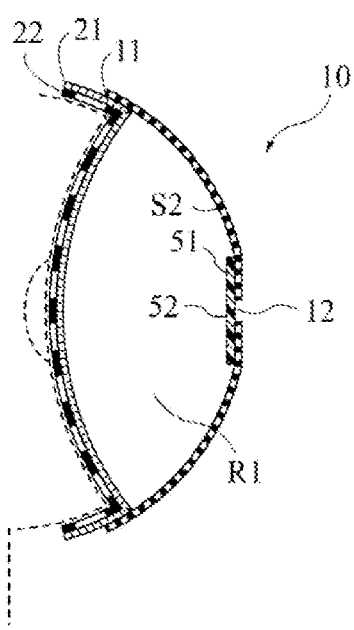
Figure 5E:
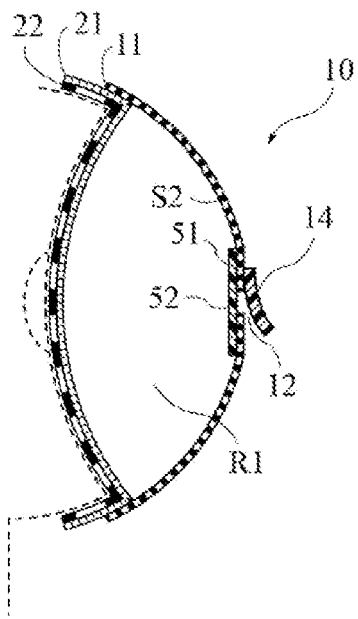

FIG. 5A to FIG. 5E show the steps of utilizing the present invention to increase the size of a breast shape visually for a female when wearing clothes. The fluid-carrying application 10 comprises a fifth sheet 51. A part of the fifth sheet 51 is connected to the second surface S2 of the first sheet 11 and is provided with a liftable part 52. The liftable part 52 is larger than the first drainage port 12 and is able to fully cover the first drainage port 12 from the inner side of the first chamber R1. Therefore, the liftable part 52 may only be lifted toward the inside of the first chamber R1 and achieves the effect of a non-return valve, and prevent the fluid from flowing from the inside of the first chamber R1 to outside through the first drainage port 12 (if a part of the fifth sheet 51 is connected to the first surface S1 of the first sheet 11, there will be a reverse effect). In step 1, as shown in FIG. 5A, the release layer 23 is separated and peeled off to expose the adhesive layer 22 on the second sheet 21. In step 2, as shown in FIG. 5B, the second sheet 21 is adhered to the breast skin with the adhesive layer 22 facing towards the breast. In step 3 (not necessary), as shown in FIG. 5C, the structure support unit 91 is removed. In step 4, as shown in FIG. 5D, an appropriate amount of water is injected through the first drainage port 12, and the hydraulic pressure inside the first chamber R1 would push the liftable part 52 towards the first drainage port 12 and therefore clog the first drainage port 12. The gradually expanding first chamber R1 causes the second sheet 21 to apply pressure on the soft tissue of the covered part of the breast in the direction towards the pectoralis major muscle, causing the breast to appear in a recessed state, while the first sheet 11 combines with the uncovered skin of the breast to form an enlarged breast shape. In step 5, as shown in FIG. 5E, the first drainage port 12 is covered with the cap 14 provided with a reusable adhesive to prevent a small amount of fluid from seeping. The water inside the first chamber R1 may combine with the user's breast through the above steps and form a natural body shape. It is also convenient for females to further adjust the volume of the breast by adjusting the amount of injected water. Since the specific gravity of water is approximately equal to the specific gravity of a human body, the characteristics of fluids may better provide the natural bounce and jiggle, and the sense of touch of the breast.

Figure 6A:
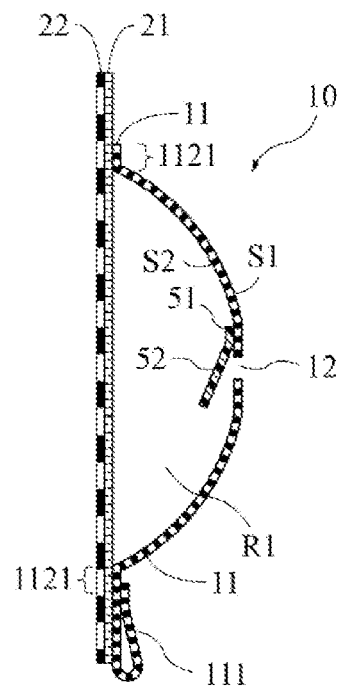
FIG. 6A to FIG. 6B are schematic diagrams of another embodiment of the fluid-carrying application.
Figure 6B:
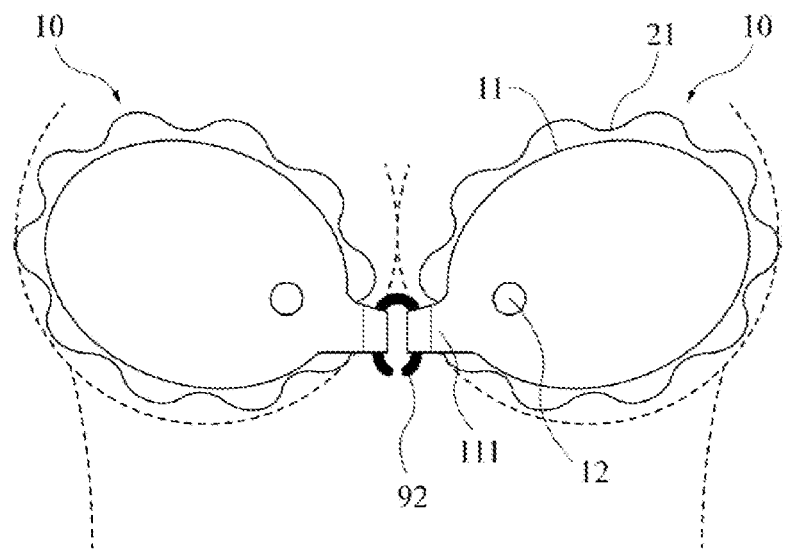

An embodiment of the present invention is shown in FIG. 6A. A piece of a part of the first sheet 11 extends outwards and forms an extending portion 111. The extending portion 111 is reversely folded and the edge of which is connected to the first sheet 11, forming into a belt. An embodiment of the present invention is shown in FIG. 6B. The first sheet 11 or the second sheet 21 is provided with undulating edges, enabling the fluid-carrying application 10 to better attach on a non-planar surface. The second sheet 21 with the undulating edge may also serve as a claw that provides a grip strength, and can better resist the external pulling force when the chamber is full of fluids. A fastener 92 may be further set up at the edge of the first sheet 11 or the second sheet 21 to connect two adjacent fluid-carrying applications 10 in a permanent or removable way. A fastener 92 may be, but is not limited to, a buckle, a button, a rivet/stud, a hasp, a zipper, a tape, a Velcro, or a binding band/rope. In the present embodiment, the fastener 92 is a C-shaped/U-shaped buckle. The two ends of the buckle pass through two aforementioned belts from the extending portion 111 of the first sheet 11 which faces towards each other, respectively, thereby shortening the distance between the two breasts, centering the breasts and boosting the cleavage visually.

Figure 7A:
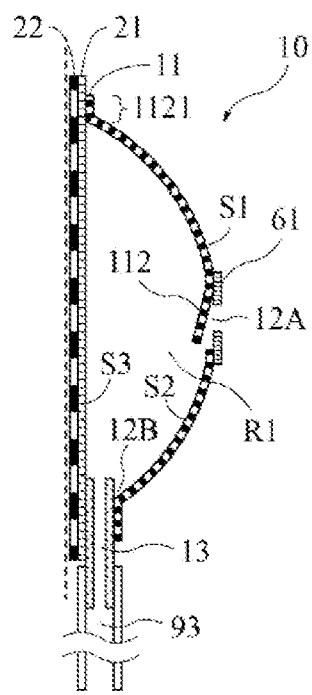
FIG. 7A to FIG. 7G are schematic diagrams of another embodiment of the fluid-carrying application.
Figure 7B:
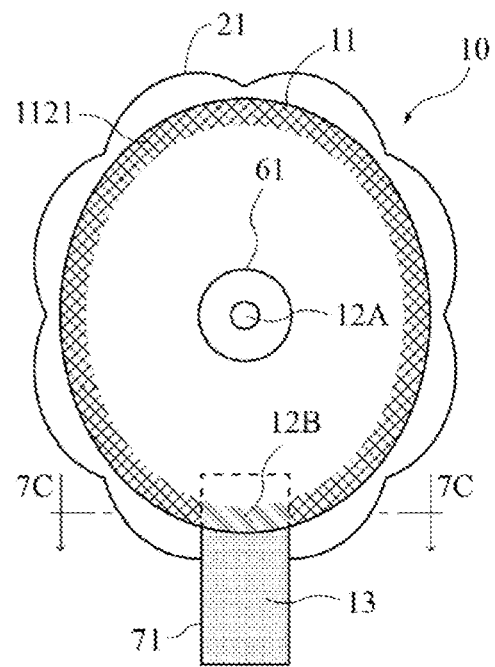
Figure 7C:
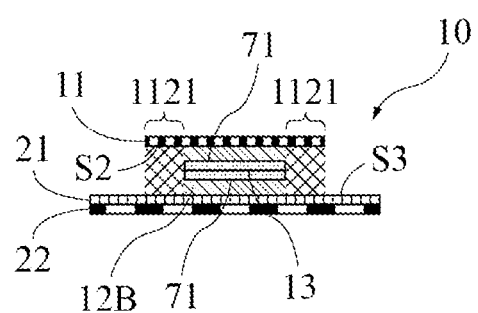
Figure 7D:
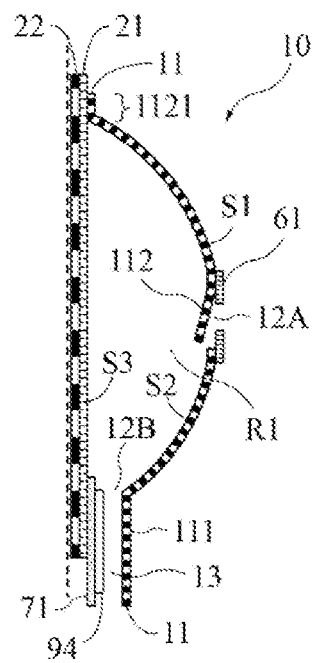
Figure 7E:
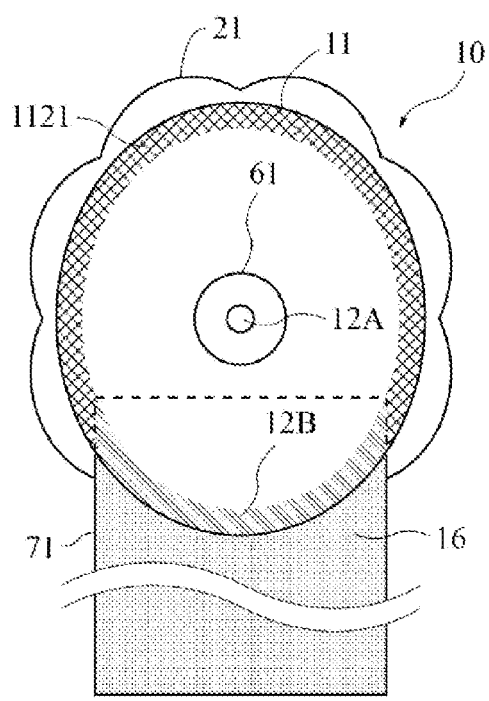
Figure 7F:
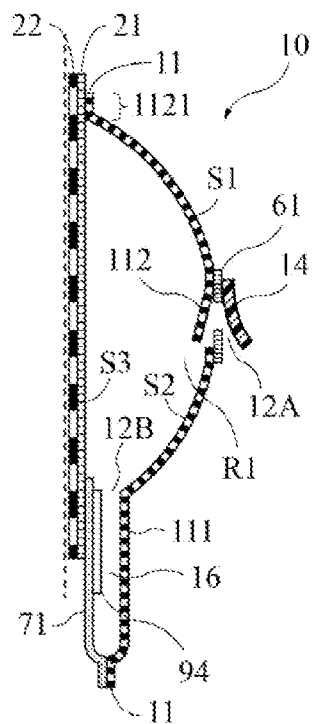
Figure 7G:
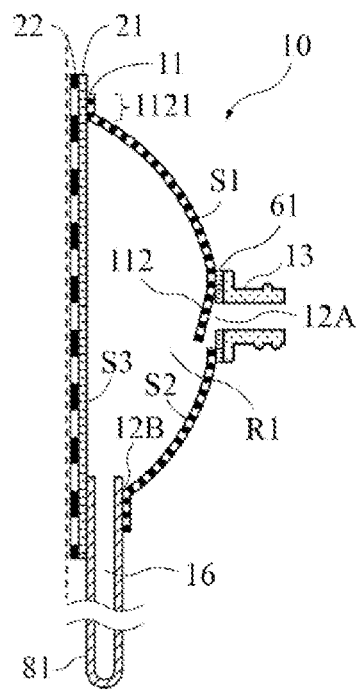

FIG. 7A to FIG. 7G show another embodiment of the present invention with two first drainage ports 12. The second sheet 21 is exemplarily shown with the same piece, where the petaloid edge achieves the same effect as the undulating edge shown in FIG. 6B, enabling the second sheet 21 to better attach on a non-planar surface. A non-return structure, a C-shaped/U-shaped first liftable part 112 formed by die-cutting the first sheet 11, forms a part of the first drainage port 12A. A sixth sheet 61 is further set up at the first drainage port 12A. The edge of the sixth sheet 61 is connected in an enclosed manner to the first surface S1 of the first sheet 11 in a form of surrounding the first liftable part 112, and is provided with an opening with the opening smaller than the first liftable part 112 and can be fully covered by the first liftable part 112 from the inner side of the first chamber R1. Therefore, the first liftable part 112 can only be lifted towards the inside of the first chamber R1 and performs the effect of a non-return valve, which prevents the fluids injected by the user from flowing from the inside of the first chamber R1 to outside through the first drainage port 12A (if the edge of the sixth sheet 61 is connected to the second surface S2 of the first sheet 11, there will be a reverse effect). As shown in FIG. 7A, an open portion is formed where the second surface S2 of the first sheet 11 and the third surface S3 adjacent to the edge of the second sheet 21 are not welded or adhered with each other, and the open portion serves as another first drainage port 12B. When a non-return structure is set up at the first drainage port 12B (not shown in the figure), the first liftable part 112 may be formed at the edge of the first sheet 11 adjacent to the first drainage port 12B, while the edge of the sixth sheet 61 is connected to the first sheet 11 and the second sheet 21 at the same time in an enclosed manner in a form of surrounding the first liftable part 112. The first drainage port 12B may further comprise a drainage portion. In the present embodiment, the drainage portion is a drainage tube 13 sandwiched between the first sheet 11 and the second sheet 21. An extending tube 93 may be further connected to the drainage tube 13 for draining. The fluid in the first chamber R1 may be drained through the first drainage port 12B, the drainage tube 13 and the extending tube 93 to the user's mouth. Thus the present invention may be provided as a water bottle adhered to the user's body for outdoor activities' use, such as long-distance running, biking, long-distance swimming or diving. Users are therefore able to drink water or consume liquid diet during the activities. Alternatively, the first chamber R1 may be formed as a flowing space with one end for injecting while the other for draining. When the present invention is used for ice packs/warm compresses, water with the same temperature may be continuously injected to keep the first chamber R1 at a constant temperature. Apart from gumming on the second sheet 21 during manufacturing, the materials composing the adhesive layer 22 may further include, for example but not limited to, a double-sided tape. One surface of the double-sided tape may be adhered to the second sheet 21 while the other surface adheres to a user, thus the first chamber R1 formed by the connection of the first sheet 11 and the second sheet 21 may be repeatedly used simply by changing the double-sided tape. FIG. 7B is a front view. The drainage tube 13 is formed by the connection of two side edges of two seventh sheets 71. The first drainage port 12B surrounds the drainage tube 13. A part of the seventh sheet 71 that is adjacent to the first drainage port 12B connects with the second surface S2 of the first sheet 11 and the third surface S3 of the second sheet 21 respectively in an enclosed manner (as shown in FIG. 7C), causing the drainage tube 13 to be flat in a natural state. The drainage tube 13 made of thin films with the thickness less than 0.1 mm may achieve an non-return effect, preventing the fluid in the first chamber R1 from draining. One of the surfaces of the drainage tube 13 that face each other is provided with an isolation material 94 (not shown in the figures), and therefore prevents the blockage of fluid flow, which results from the melting and bonding of the inner surfaces (apart from the two side edges) of the seventh sheet 71 due to the heat during the manufacturing. The isolation material 94 is sandwiched, coated or printed before the drainage tube 13 is formed by the connection of the two sheets. An isolation material 94 is set up at a part of the seventh sheet 71 that is adjacent to the second sheet 21 (as shown in FIG. 7D). In the present embodiment, the first sheet 11 may further comprise an extending portion 111, which replaces the seventh sheet 71 that connects to the first sheet 11 (that is, the first sheet 11 and the seventh sheet 71 are formed integrally), thus forming a drainage tube 13. FIG. 7E is a front view. The drainage portion is a drainage bag 16 being set up correspondingly to the first drainage port 12B. Similar with the drainage tube 13 in FIG. 7B, the drainage bag 16 is formed by connecting the two side edges of the two seventh sheets 71 as well as the bottom edge. The volume of the drainage bag 16 may be increased by widening and lengthening the seventh sheet 71. As shown in FIG. 7F, the drainage bag 16 is similar to the drainage tube 13 in FIG. 7D. The seventh sheet 71 adjacent to the first sheet 11 may be replaced by extending the first sheet 11. The end of the extending portion 111 of the first sheet 11 is connected with the bottom edge of the seventh sheet 71. The top edge of the seventh sheet 71 is connected with the second sheet 21. The drainage bag 16 is formed by connecting the two open side edges of the extending portion 111 and the seventh sheet 71. An isolation material 94 is provided on either the surface of the seventh sheet 71 that faces the extending portion 111, or the surface of the extending portion 111 that faces the seventh sheet 71. The opening of the sixth sheet 61 is further covered with a cap 14 provided with a reusable adhesive, preventing a small amount of fluid from seeping. As shown in FIG. 7G, the drainage bag 16 is formed by folding an eighth sheet 81 in half and sealing all or part of the edges of the eighth sheet 81. In the present embodiment, a drainage tube 13 is further being set up correspondingly to the opening of the sixth sheet 61.

Figure 8A:
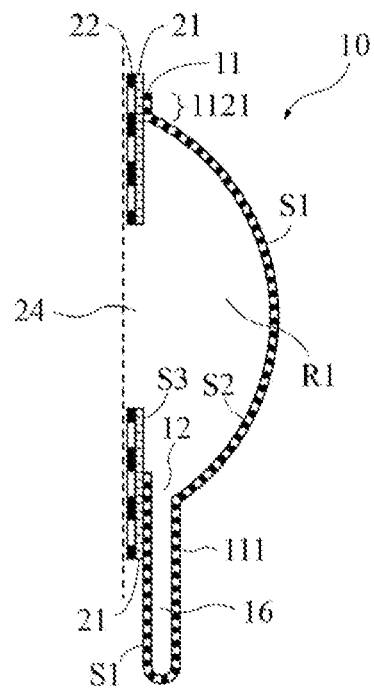
FIG. 8A to FIG. 8C are schematic diagrams of another embodiment of the fluid-carrying application.
Figure 8B:
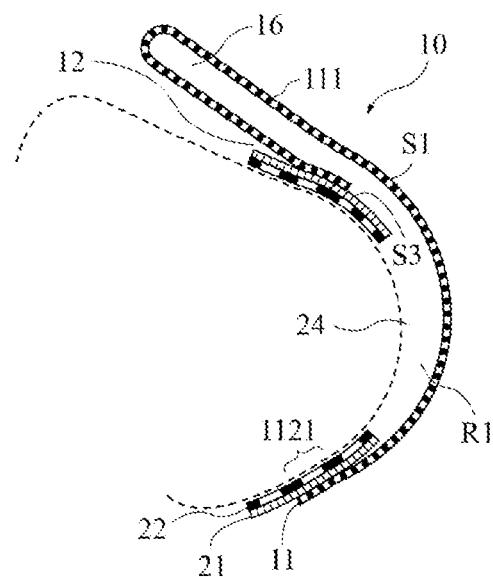
Figure 8C:
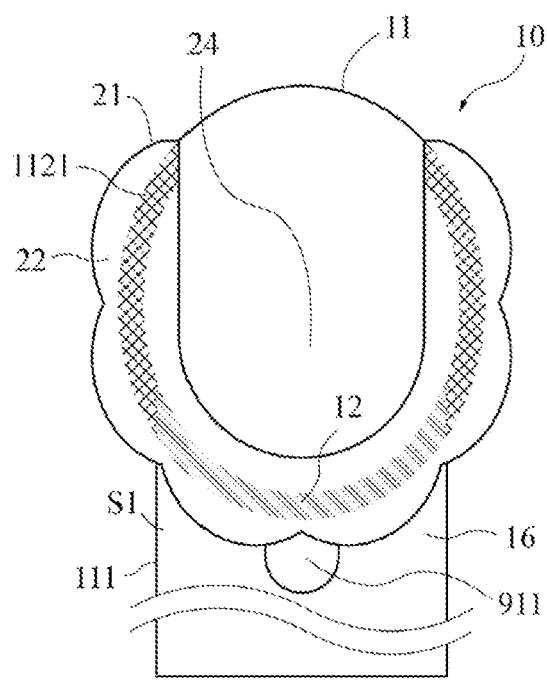

FIG. 8A to FIG. 8C show another embodiment of the present invention. A first drainage port 12 is formed at an open portion where the first sheet 11 and the part adjacent to the edge of the second sheet 21 are not welded or adhered to each other. As shown in FIG. 8A, the half-folded eighth sheet 81 in FIG. 7G is further replaced by the extending portion 111 of the first sheet 11 to form a drainage bag 16. The drainage bag 16 is formed by connecting the first surface S1 of the extending first sheet 11 and the third surface S3 of the second sheet 21, and then connecting the two open side edges of the half-folded extending portion 111. Meanwhile, the second sheet 21 is provided with at least a second drainage port 24, which enables the inside of the first chamber R1 to communicate with the outside through the second drainage port 24. The second drainage port 24 is smaller than the inner edge of the band-shaped region 1121, thereby forming a distance between the second drainage port 24 and the inner edge of the band-shaped region 1121. The distance is preferably greater than 3 mm, more preferably greater than 8 mm, and most preferably greater than 15 mm. When the present invention is used as a semen collection device, the thickness of the first sheet 11, the second sheet 21 and the seventh sheet 71 is preferably less than 0.05 mm, more preferably less than 0.03 mm, most preferably less than 0.02 mm. The perimeter of the second sheet 21 is preferably less than 180 mm, more preferably less than 150 mm, most preferably less than 120 mm. The widest part of the second sheet 21 is preferably less than 60 mm, more preferably less than 55 mm, most preferably less than 50 mm. The volume of the drainage bag 16 is preferably less than 20 ml, more preferably less than 15 ml, most preferably less than 10 ml. Lesser perimeter and thickness of the sheet can create a smaller and thinner body fluid collection device 10, so as to increase pleasure during sexual intercourse. The volume is set with reference to the fact that the amount of sperm per ejaculate by male is generally no more than 10 ml. FIG. 8B shows another embodiment of the present invention for semen collection. Since the coronal sulcus adjacent to the frenulum of prepuce is the part that bears the strongest friction during thrusting activity, the first sheet 11 and the second sheet 21 in this area are connected with each other with the U-shaped/C-shaped band-shaped region 1121. The first chamber R1 is generally in a closed state during sexual intercourse, effectively preventing the first sheet 11 and the second sheet 21 from peeling off due to a pulling force that is caused by friction. FIG. 8C is a back view (also referring to FIG. 8A), where the second drainage port 24 extends from the center of the second sheet 21 to the top edge of the second sheet 21, forming the second sheet 21 with an opened and U-shaped (or C-shaped/V-shaped) upper end. When in use, by adhering the fluid-carrying application 10 to a bedridden female's pudendum with the open end facing towards the female's pubis bones, the urine sample may be collected directly instead of using a catheter in an invasive method. The second sheet 21 with the design of an open end may prevent the difficulty in removing, which is caused by the adhesive layer 22 sticking to body hairs. The structure support unit 91 (not shown in the figure) may further extend outwards from the edge to form a pinch portion 911 protruding from the second sheet 21. At least one point of the pinch portion 911 is connected to the structure support unit 91 for the ease of the user to adjust the position of the fluid-carrying application of the present invention before adhesion, or to remove the structure support unit 91 after adhesion while pinching with fingers.

Figure 9A:
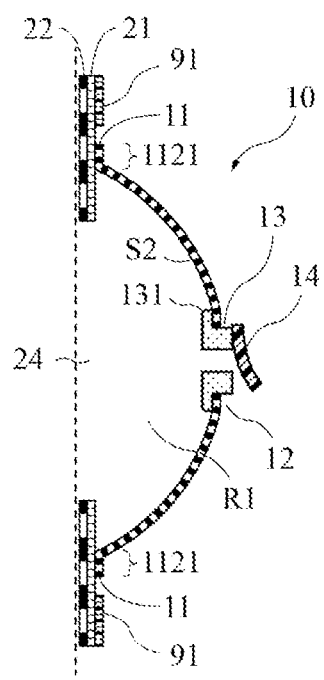
FIG. 9A to FIG. 9C are schematic diagrams of another embodiment of the fluid-carrying application.
Figure 9B:
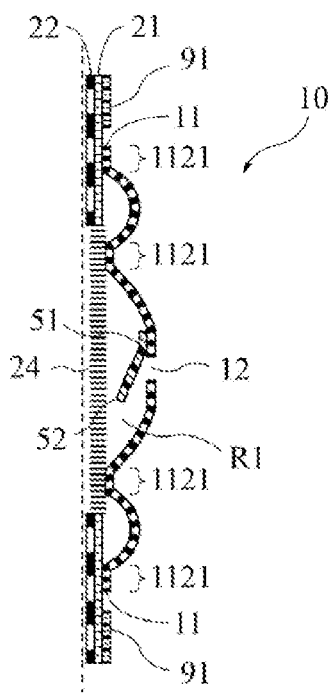
Figure 9C:
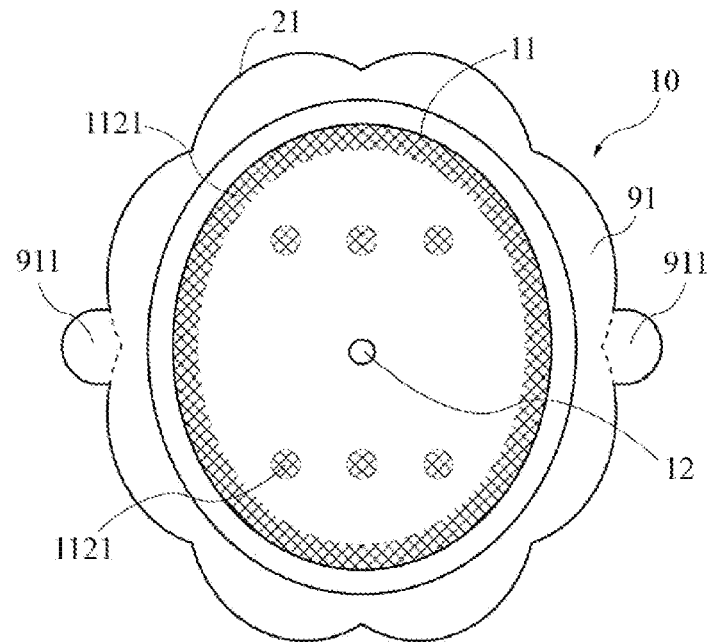

FIG. 9A to FIG. 9C show another embodiment of the present invention. As shown in FIG. 9A, the drainage tube 13 has a wider cross section of the tube wall and an outer cross section generally same as the first drainage port 12. The cap 14 or the cross section of the tube wall of one end of the drainage tube 13 is provided with a reusable adhesive, thereby the cap 14 is adhered to the drainage tube 13 in a removable way. Meanwhile, the second sheet 21 is provided with at least a second drainage port 24. The user may inject drugs or skin care products through the drainage tube 13. The fluid in the first chamber R1 may therefore contact the body surface directly through the second drainage port 24, and the drugs or skin care products may be directly introduced to wounds or can be used to moisten skins directly. For the drugs that are absorbed through skins, the effect of preventing the loss of the drugs or avoiding clothes being stained may also be achieved. If there is the need to ease the effect of the fluid on bodies, a unidirectional or bidirectional osmosis membrane may be set up at the second drainage port 24 (as shown in FIG. 9B), such as gauze or meltblown nonwoven fabric. Alternatively, a plurality of second drainage ports 24 may be formed by processing at least a part of the second sheet 21. Small and densely arranged openings enable the fluid to slowly permeate through the microporous membrane. Alternatively, when the user injects fluid, the liftable part 52 of the fifth sheet 51 may prevent the fluid from flowing out. A plurality of spotted/ribboned band-shaped regions 1121 may be further set up at the range of the first chamber R1 (as shown in FIG. 9C, which is the front view of FIG. 9B) to form a plurality of small chambers that can communicate with one another in the first chamber R1. The distance between the first sheet 11 and the second sheet 21 is shorter (as shown in FIG. 9B), so that the best effect of immersion may be achieved by lesser fluids. Two side edges of the structure support unit 91 may be further provided with pinch portions 911 correspondingly for a user to operate at ease.

Figure 10:
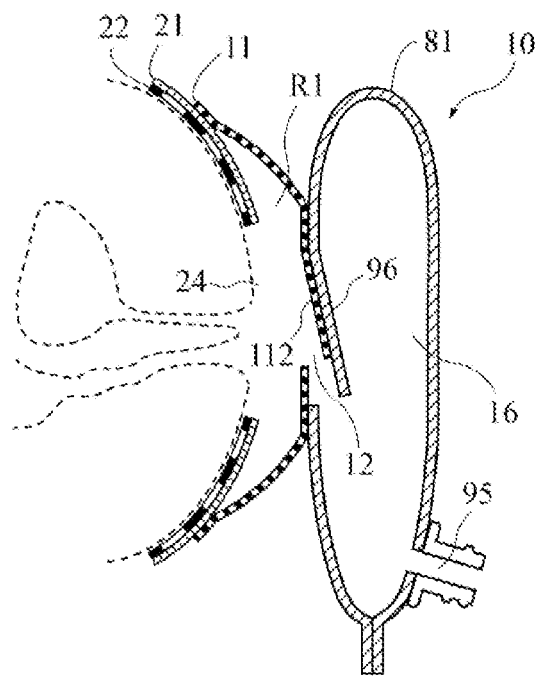
FIG. 10 is a schematic diagram of another embodiment of the fluid-carrying application.

FIG. 10 is another embodiment of the present invention. The second sheet 21 is provided with a second drainage port 24. The drainage portion is a drainage bag 16 being set up correspondingly to the first drainage port 12. The drainage bag 16 may be formed by combining two seventh sheets 71, which is shown in FIG. 7E, or it may be as shown in the present embodiment, formed by folding the eighth sheet 81 in half and sealing all or part of the edges of the eighth sheet 81. The edges of the eighth sheet 81 may be further provided with an unsealed open portion to form a drainage port of the drainage bag 16. When in use, the second drainage port 24 is aligned with the urethral orifice and ostium vaginae of a female user, and the second sheet 21 is adhered to the vulva using the adhesive layer 22, so that urine or menstrual blood may flow into the drainage bag 16 for storage. The drainage bag 16 may be further provided with a second drainage tube 95 for timely discharging body fluids. Additionally, the drainage bag 16 of the present embodiment may further comprise a structure with an non-return effect, and can prevent the fluid in the drainage bag 16 from flowing back to the first chamber R1. As shown in FIG. 10, the first sheet 11 comprises a first liftable part 112. The eight sheet 81, which forms the drainage bag 16, comprises a second liftable part 96 larger than the first liftable part 112. The first sheet 11 and the eighth sheet 81 are connected in a enclosed manner in the form of surrounding the first liftable part 112 and the second liftable part 96. At least a part of the first liftable part 112 is connected to the second liftable part 96 (welded or adhered). Since the size of the first liftable part 112 is smaller than the second liftable part 96, the connection of the two parts may only be lifted towards the inside of the drainage bag 16. Therefore, an effect of preventing backflow of the fluid in the drainage bag 16 may be achieved. It may be understood by those of ordinary skill in the art that if the drainage bag 16 is formed by two seventh sheets 71, the seventh sheet 71 may likely be provided with a second liftable part 96 to prevent the fluid from flowing back.

Figure 11:
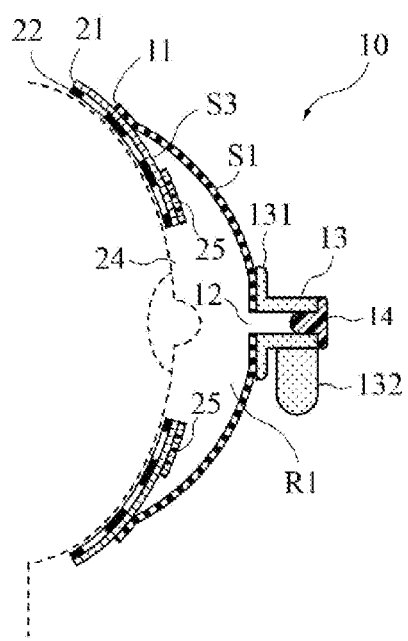
FIG. 11 is a schematic diagram of another embodiment of the fluid-carrying application.

FIG. 11 is another embodiment of the present invention. A flat operating portion 132 may be further set up at the drainage tube 13, so that the user may open or close the drainage tube 13 with one hand fixing the drainage 13 and the other operating the cap 14. When in use, the release layer 23 is first separated and peeled off. The second drainage port 24 is aligned with a nipple of a female and the second sheet 21 is adhered to the breast skin with the adhesive layer 22. The cap 14 is then plugged into the drainage tube 13 by means of the elasticity and friction of material and close the drainage tube 13. The user's milk may flow from the second drainage port 24 to the first chamber R1 and store in the first chamber R1. Then the user opens the drainage tube 13 to discharge the body fluid after selecting an appropriate place. The present invention may help breastfeeding mothers prevent staining clothes or unpleasant odor due to galactorrhea. When the second sheet 21 is adhered to a body surface that is arc-shaped, irregular fluctuated or fat, wrinkles are easily formed at the edge of the second drainage port 24. Due to hydraulic pressure, fluids would leak from small channels formed at wrinkled area towards the edge of the second sheet 21, eventually the second sheet 21 would peel off due to a gradually decreased adhesive strength of the adhesive layer 22. Therefore, a structure support unit of the drainage port 25 may be further set up extending along the third surface S3 of the second sheet 21 and the edge surrounding the second drainage port 24 to maintain the shape of the second drainage port 24 and avoid leakage. By adjusting the adhesiveness of the structure support unit of the drainage port 25 (for example, by making the adhesiveness between the structure support unit of the drainage port 25 and the second sheet 21 weaker than the adhesiveness between the second sheet 21 and the human body through the adhesive layer 22), after the second sheet 21 is adhered to the body surface, when the body surface forms wrinkles on the second sheet 21 due to squeezing or friction, the structure support unit of the drainage port 25 would peel off from the second sheet 21 due to the weak adhesiveness, therefore does not affect the adhesion between the edge of the second drainage port 24 and the body surface.

Figure 12A:
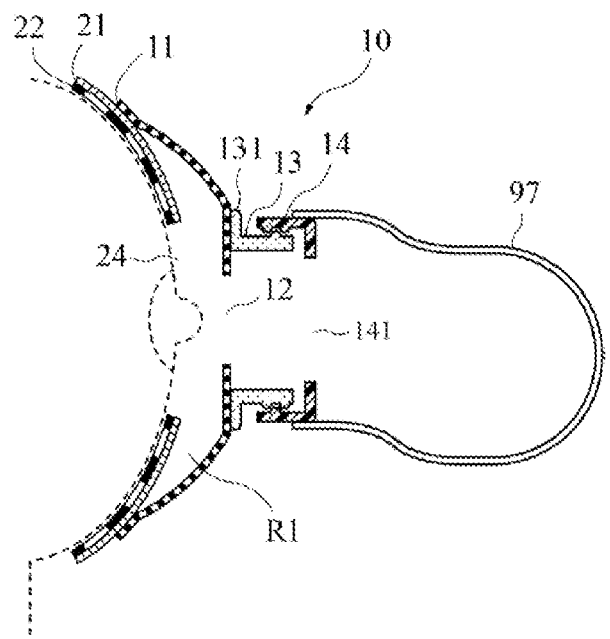
FIG. 12A and FIG. 12B are schematic diagrams of another embodiment of the fluid-carrying application.
Figure 12B:
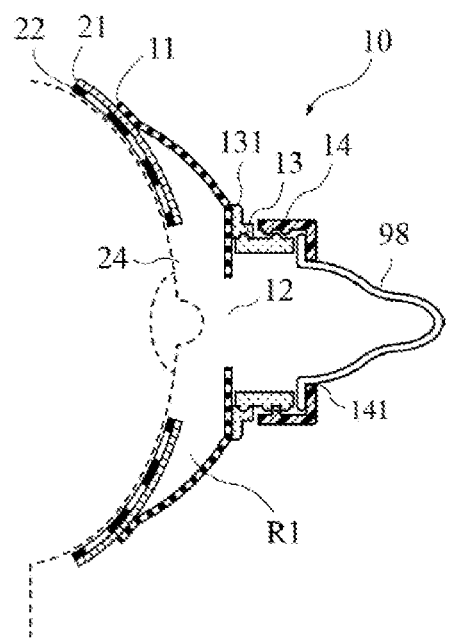

The embodiment of the present invention shown in FIG. 12A and FIG. 12B is for breastfeeding. The fluid-carrying application 10 is provided with detachable structures, such as but not limited to, an extending tube, a drainage bag, a pacifier or a valve. Referring to FIG. 12A, the second sheet 21 is provided with a second drainage port 24. The drainage tube 13 is provided with an inner cross sectional area larger than the first drainage port 12, so that the first chamber R1 has a better effect of sealing and leakproof. Additionally, the cap 14 may be further connected to a second drainage bag 97. The second drainage bag 97 is set up correspondingly to a drainage port on the cap 141 on the cap 14, therefore when the cap 14 is locked with the drainage tube 13, the inside of the first chamber R1 is in communication with the inside of the second drainage bag 97 through the first drainage port 12, the drainage tube 13 and the drainage port on the cap 141, which may help breastfeeding mothers in milking and storing the milk. It may be understood by those of ordinary skill in the art that in the present embodiment, a second drainage bag 97 may also be directly connected to the drainage tube 13 for storing body fluids. As shown in FIG. 12B, a pacifier 98 may be further sandwiched between the drainage tube 13 and the cap 14, in order to prevent the pain and damage of nipples due to breastfeeding. In the present embodiment, the cap 14 may also be connected to a valve, a cover, a switch or a sticker for opening or closing the drainage port on the cap 141 and discharging the milk to prevent clothes from staining due to galactorrhea. Alternatively, the cap 14 may be further connected to an extending tube 93 in order to drain the milk to a distal container. The set up of the brim portion 131 surrounding one end of the drainage tube 13 may be in the manner that, for example but not limited to, one of the brim portion 131 and the drainage tube 13 is provided with a flange and the other is provided with a concave flange so that the two are fixed with each other (as shown in FIG. 12B), the brim portion 131 and the drainage tube 13 are threadedly fixed with each other, the brim portion 131 and the drainage tube 13 are connected and formed integrally, or one of the brim portion 131 and the drainage tube 13 is plugged into the other by means of material elasticity and friction.

Figure 13:
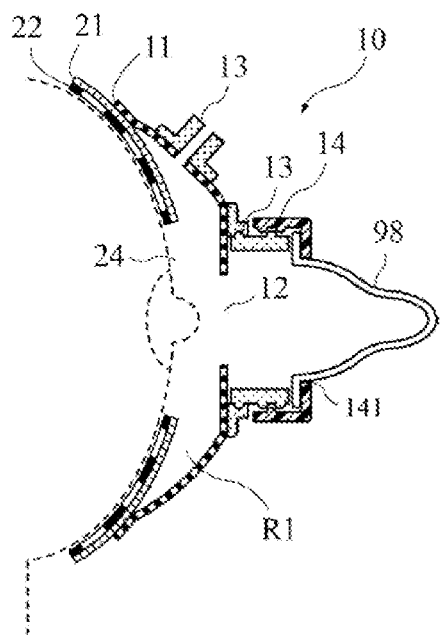
FIG. 13 is a schematic diagram of another embodiment of the fluid-carrying application.

FIG. 13 is another embodiment of the present invention. Also referring to FIG. 12B, apart from a drainage tube 13 that comprises a detachable pacifier 98 and a cap 14, another drainage tube 13 may be further set up on the first sheet 11 for injecting cow's milk and thus can help mothers with low milk supply. The second sheet 21 may be provided with a second drainage port 24, so that the breast milk may flow into the first chamber R1 simultaneously. The second sheet 21 may also be a continuously closed sheet, so that a user who does not produce milk (such as fathers) may also feed babies.

Figure 14:
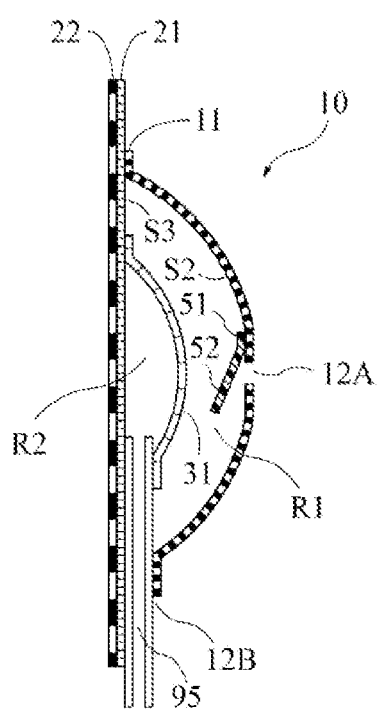
FIG. 14 is a schematic diagram of another embodiment of the fluid-carrying application.

FIG. 14 is another embodiment of the present invention. Also referring to FIG. 2C and FIG. 5A, apart from the liftable part 52 covering the first drainage port 12A, the fluid-carrying application 10 may be further provided with a third sheet 31 between the first sheet 11 and the second sheet 21. The edge of the third sheet 31 is welded/adhered to the second sheet 21, thereby forming a second chamber R2 between the third sheet 31 and the second sheet 21 (separated from the original first chamber R1). The part where the third surface S3 of the second sheet 21 and the edge of the third sheet 31 are not welded or adhered with each other forms an open portion, which is further connected to a second drainage tube 95. The drainage tube 95 is sandwiched between the second sheet 21 and the third sheet 31 and passes through another first drainage port 12B, so that the inside of the second chamber R2 may be in communication with the outside through the second drainage tube 95. When in use, the user may first adhere the fluid-carrying application 10 to the breast, inject air into the second chamber R2 through the second drainage tube 95, and then inject water into the first chamber R1 through the first drainage port 12A. It may not only increase the size of the breast visually when the user wears clothes, but also alleviate the burden on the chest. It should be understood by those of ordinary skill in the art that the second drainage tube 95 may also be connected to a second drainage port 24 on the second sheet 21 (not shown in the figures). In the present embodiment, the second sheet 21 for adhering to the breast is a flat film, the third sheet 31 may be made of a flat or arc-shaped film, and the first sheet 11 is preferably made of an arc-shaped film.

Figure 15A:
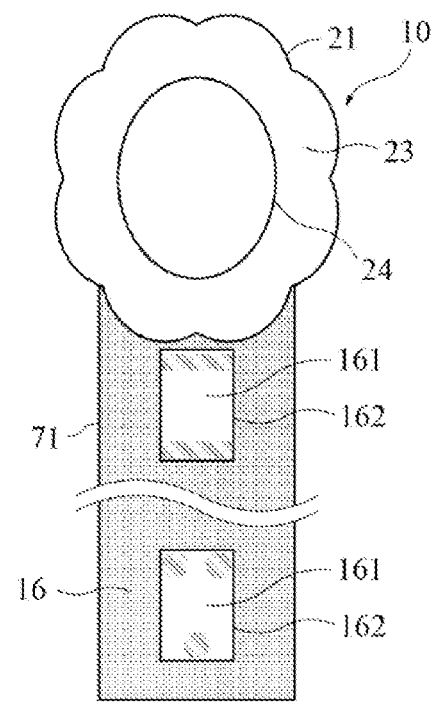
FIG. 15A and FIG. 15B are schematic diagrams of another embodiment of the fluid-carrying application.
Figure 15B:
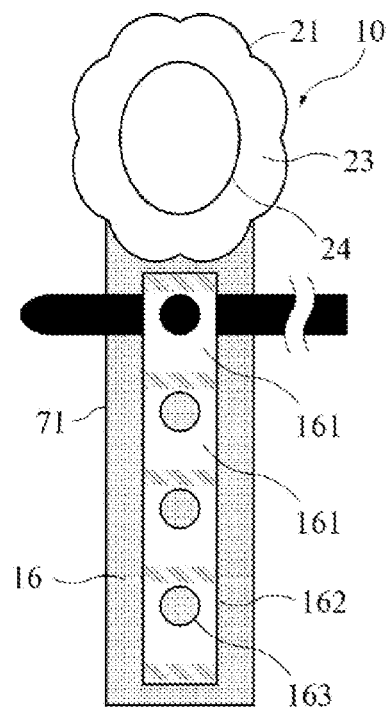

FIG. 15A and FIG. 15B show another embodiment of the present invention. Also referring to FIG. 7E to FIG. 7G, FIG. 8A and FIG. 10, as shown in FIG. 15A (FIG. 15A is the back view of FIG. 7E where a second sheet 21 is further processed into a second drainage port 24), one embodiment of the fluid-carrying application 10 of the present invention is further providing a belt loop 161 on the drainage bag 16. A fixing rope or a fixing belt may pass through the belt loop passage formed between the belt loop 161 and the drainage bag 16, and thus the drainage bag 16 may be fixed on a part of the user's body. The drainage bag 16 may be further provided with a plurality of belt loops 161 so that the user may choose different fixing positions. As shown in FIG. 15A, when the drainage bag 16 is generally being set up parallel to legs, a plurality of belt loops 161 may be set up in a vertical direction, thus enhancing the stability of the drainage bag 16 as well as enabling the user to choose different belt loop passages to adjust and achieve the best fixing way. The belt loop 161 may be formed in the manner of, for example, connecting a belt loop sheet 162 with the drainage bag 16 by welding or adhering (but not limited to the above manner). For example, as shown in FIG. 15A, if the belt loop sheet 162 is rectangular, two opposite sides of the rectangle may be connected to the drainage bag 16, or two or more points in the scope of the rectangle may be connected to the drainage bag 16. Alternatively, as shown in FIG. 15B, by using and connecting a long-strip belt loop sheet 162 to three or more points of the drainage bag 16 along the long side of the long-strip belt loop sheet 162, a plurality of belt loop passages may be formed. A button hole 163 may be further set up on the belt loop sheet 162 correspondingly to every belt loop passage. In combination with the fasteners on the fixing belt, the drainage bag 16 may be prevented from shifting along the fixing rope or the fixing belt.

Figure 16:
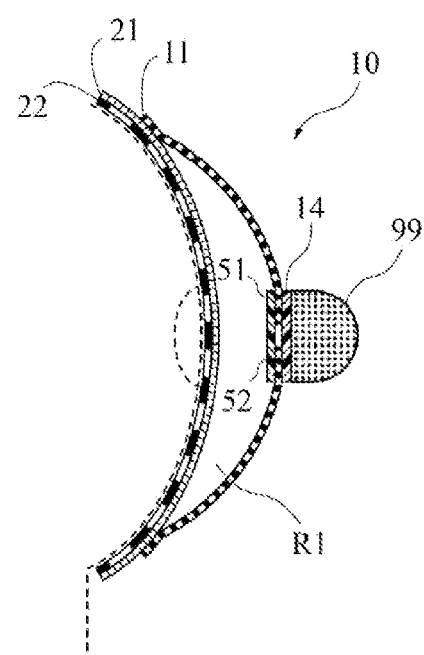
FIG. 16 is a schematic diagram of another embodiment of the fluid-carrying application.

FIG. 16 is another embodiment of the present invention. The fluid-carrying application 10 further comprises a pulse portion 99, which can keep the mammary gland unobstructed and help produce milk by applying pulse vibration massages on breasts. The pulse portion 99 is preferably set up on the first sheet 11, and may be, for example, connected to a cap 14, especially a cap 14 provided with a reusable adhesive (referring to FIG. 5E and FIG. 9A). The pulse portion 99 may be provided with a vibration device or a discharge device set up on the first sheet 11. Furthermore, with good conduction properties of the fluid in the first chamber, the pulsed vibration or the pulsed current would be more effectively and evenly conducted to the body surface covered by the second sheet 21 or the second drainage port 24. Therefore, a better effect of massage may be achieved by the pulsed vibration, or a better effect of electrotherapy may be achieved by the pulsed current, or the drugs or skin care products in the first chamber R1 may be better absorbed by the body surface.

The above descriptions are only examples, not limitations. Any equivalent modifications or variations made without disengaging from the spirit and scope of the present invention all falls within the scope of the appended claims.

What is claimed is:

1. A fluid-carrying application (10), comprising:
a first sheet (11), provided with a first surface (S1) and a second surface (S2);
a second sheet (21), provided with a third surface (S3) and a fourth surface (S4), a part of the third surface (S3) and a part of the second surface (S2) of the first sheet (11) are welded or adhered to at least one band-shaped region (1121), thereby forming a first chamber (R1) having at least a first drainage port (12), and an inside of the first chamber (R1) can communicate with an outside through the first drainage port (12);
an adhesive layer (22), provided on the fourth surface (S4) of the second sheet (21); and
a release layer (23), covering at least a part of the adhesive layer (22);
wherein the first drainage port (12) is formed at the first sheet (11) or an open portion where the second surface (S2) of the first sheet (11) and the third surface (S3) adjacent to an edge of the second sheet (21) are not welded or adhered to each other.

2. The fluid-carrying application (10) according to claim 1, wherein a third sheet (31) is provided between the first sheet (11) and the second sheet (21), a second chamber (R2) is formed between the third sheet (31) and the second sheet (21), and edges of the third sheet (31) may be welded or adhered in between the first sheet (11) and the second sheet (21) at the same time, or to the first sheet (11), or to the second sheet (21).

3. The fluid-carrying application (10) according to claim 1, wherein the edge of the second sheet (21) is larger than an outer edge of the band-shaped region (1121), and there is a distance between the outer edge of the band-shaped region (1121) and the edge of the second sheet (21).

4. The fluid-carrying application (10) according to claim 1, further comprising a fifth sheet (51), a part of the fifth sheet (51) is connected to a surface of the first sheet (11) and provided with a liftable part (52), the liftable part (52) being larger than the first drainage port (12) and may fully cover the first drainage port (12).

5. The fluid-carrying application (10) according to claim 1, wherein the first drainage port (12) further comprises a first liftable part (112) of the first sheet (11), and the surface of the first sheet (11) further comprises a sixth sheet (61), an edge of the sixth sheet (61) is connected to the first sheet (11) in an enclosed manner in a form of surrounding the first liftable part (112) of the first sheet (11), or connected to the first sheet (11) and the second sheet (21) at the same time and comprises an opening, with the opening being smaller than the first liftable part (112) of the first sheet (11) and may be fully covered by the first liftable part (112).

6. The fluid-carrying application (10) according to claim 1, wherein the second sheet (21) is provided with at least a second drainage port (24).

7. The fluid-carrying application (10) according to claim 1, wherein the material constituting the adhesive layer (22) includes a pressure-sensitive adhesive or a replaceable double-sided tape.

8. The fluid-carrying application (10) according to claim 1, further comprising a drainage tube (13) or a drainage bag (16), with the drainage tube (13) or the drainage bag (16) connected to the first drainage port (12) or an opening of a sixth sheet (61).

9. The fluid-carrying application (10) according to claim 8, wherein the drainage tube (13) or the drainage bag (16) further comprises a non-return structure, which can prevent the fluid from flowing through the drainage tube (13) or the drainage bag (16) from the inside of the first chamber (R1) to the outside or from the outside of the first chamber (R1) to the inside.

10. The fluid-carrying application (10) according to claim 8, wherein the drainage tube (13) comprises a cap (14), and the drainage tube (13) is configured to be opened or closed in one of the following manners:
the cap (14) and the drainage tube (13) are threadedly locked with each other;
one of the cap (14) and the drainage tube (13) is provided with a flange and the other is provided with a concave flange, allowing the cap (14) and the drainage tube (13) to be fixed with each other;
one of the cap (14) and the drainage tube (13) is plugged into the other by means of material elasticity and friction;
at least one of the cap (14) and the drainage tube (13) is provided with a reusable adhesive to adhere the cap (14) to the drainage tube (13) in a removable way.

11. The fluid-carrying application (10) according to claim 8, wherein the drainage tube (13) is formed by combining two side edges of two seventh sheets (71), causing the drainage tube (13) to be flat in a natural state.

12. The fluid-carrying application (10) according to claim 8, wherein an inner surface of the drainage tube (13) or the drainage bag (16) is provided with an isolation material (94), which is sandwiched, coated or printed before the drainage tube (13) or the drainage bag (16) is formed.

13. The fluid-carrying application (10) according to claim 8, wherein the drainage bag (16) is formed by sealing all or part of the edges of two seventh sheets (71), or by folding an eighth sheet (81) in half and sealing all or part of the edges of the eighth sheet (81).

14. The fluid-carrying application (10) according to claim 1, wherein the first sheet (11) comprises an extending portion (111).

15. The fluid-carrying application (10) according to claim 1, wherein an edge of the first sheet (11) or the second sheet (21) is provided with a fastener (92) to connect to another fluid-carrying application (10).

16. The fluid-carrying application (10) according to claim 1, wherein at least a part of the second sheet (21) is an air-permeable or liquid-permeable sheet.

17. The fluid-carrying application (10) according to claim 6, wherein the distance of the widest part between an outer edge of the band-shaped region (1121) and the edge of the second sheet (21) is greater than 3 mm, and the distance between an inner edge of the band-shaped region (1121) and the second drainage port (24) is greater than 3 mm.

18. A fluid-carrying application (10), comprising:
a first sheet (11), provided with a first surface (S1) and a second surface (S2);
a second sheet (21), provided with a third surface (S3) and a fourth surface (S4), a part of the third surface (S3) and a part of the second surface (S2) of the first sheet (11) are welded or adhered to at least one band-shaped region (1121), thereby forming a first chamber (R1) having at least a first drainage port (12), and an inside of the first chamber (R1) can communicate with an outside through the first drainage port (12), wherein the second sheet (21) is provided with at least a second drainage port (24);
an adhesive layer (22), provided on the fourth surface (S4) of the second sheet (21);
a structure support unit of a drainage port (25), which extends along an edge of the second drainage port (24) with an adhesive strength weaker than the adhesive layer (22); and
a release layer (23), covering at least a part of the adhesive layer (22);
wherein the first drainage port (12) is formed at the first sheet (11) or an open portion where the second surface (S2) of the first sheet (11) and the third surface (S3) adjacent to an edge of the second sheet (21) are not welded or adhered to each other.

19. The fluid-carrying application (10) according to claim 18, further comprising a drainage tube (13) or a drainage bag (16), with the drainage tube (13) or the drainage bag (16) connected to the first drainage port (12).

20. The fluid-carrying application (10) according to claim 19, wherein the first sheet (11) comprises a first liftable part (112), the drainage bag (16) comprises a second liftable part (96) that is larger than the first liftable part (112), the first sheet (11) is connected to the drainage bag (16) in an enclosed manner in a form of surrounding the first liftable part (112) and the second liftable part (96), and the first liftable part (112) is connected to part of the second liftable part (96).

21. The fluid-carrying application (10) according to claim 19, further comprising a belt loop sheet (162), which is connected to the outer side of the drainage bag (16) and thus forms a passage for a fixing belt to pass through.

22. A fluid-carrying application (10), comprising:
a first sheet (11), provided with a first surface (S1) and a second surface (S2);

a second sheet (21), provided with a third surface (S3) and a fourth surface (S4), a part of the third surface (S3) and a part of the second surface (S2) of the first sheet (11) are welded or adhered to at least one band-shaped region (1121), thereby forming a first chamber (R1) having at least a first drainage port (12), and an inside of the first chamber (R1) can communicate with an outside through the first drainage port (12), wherein the second sheet (21) is provided with at least a second drainage port (24);

a drainage bag (16) being set up at the first drainage port (12), the drainage bag (16) is formed by sealing all or part of the edges of two seventh sheets (71), or by folding an eighth sheet (81) in half and sealing all or part of the edges of the eighth sheet (81);

an adhesive layer (22), provided on the fourth surface (S4) of the second sheet (21); and a release layer (23), covering at least a part of the adhesive layer (22);

wherein the first drainage port (12) is formed at the first sheet (11) or an open portion where the second surface (S2) of the first sheet (11) and the third surface (S3) adjacent to the edge of the second sheet (21) are not welded or adhered to each other.

23. The fluid-carrying application (10) according to claim 22, wherein an inner surface of the drainage bag (16) is provided with an isolation material (94), which is sandwiched, coated or printed before the drainage bag (16) is formed.

24. The fluid-carrying application (10) according to claim 22, further comprising a belt loop sheet (162), which is connected to the outer side of the drainage bag (16) and thus forms a passage for a fixing belt to pass through.

25. The fluid-carrying application (10) according to claim 22, wherein the first sheet (11) comprises an extending portion (111), which replaces the seventh sheet (71) or the eighth sheet (81) to form the drainage bag (16).

* * * * *